(12) United States Patent
Cottrell et al.

(10) Patent No.: US 7,927,379 B2
(45) Date of Patent: Apr. 19, 2011

(54) METHOD FOR FABRIC TREATMENT AT LOW PH

(75) Inventors: Stephanie Nussbaum Cottrell, Denver, NC (US); Tirthankar Ghosh, Oreland, PA (US)

(73) Assignee: Rohm and Haas Company, Philadelphia, PA (US)

( * ) Notice: Subject to any disclaimer, the term of this patent is extended or adjusted under 35 U.S.C. 154(b) by 0 days.

(21) Appl. No.: 12/717,207

(22) Filed: Mar. 4, 2010

(65) Prior Publication Data

US 2010/0229311 A1 Sep. 16, 2010

Related U.S. Application Data

(60) Provisional application No. 61/209,822, filed on Mar. 11, 2009.

(51) Int. Cl.
*C11D 3/00* (2006.01)
*C11D 3/395* (2006.01)
*B32B 5/02* (2006.01)
*B32B 27/04* (2006.01)
*B32B 27/12* (2006.01)
*B32B 9/04* (2006.01)
*B32B 27/02* (2006.01)

(52) U.S. Cl. ....... 8/115.51; 442/123; 442/153; 442/164; 510/199

(58) Field of Classification Search ................. 8/115.51; 442/123, 153, 164; 510/199
See application file for complete search history.

(56) References Cited

U.S. PATENT DOCUMENTS

| | | | |
|---|---|---|---|
| 4,996,052 A | 2/1991 | McIntosh | |
| 6,469,097 B1 | 10/2002 | Bett et al. | |
| 7,335,613 B2 * | 2/2008 | Cottrell et al. | 442/123 |
| 7,390,774 B2 * | 6/2008 | Ghosh et al. | 510/199 |
| 2005/0226914 A1 | 10/2005 | Cottrell et al. | |
| 2005/0227895 A1 | 10/2005 | Ghosh et al. | |
| 2007/0082935 A1 | 4/2007 | Chia et al. | |
| 2008/0115291 A1 | 5/2008 | Cottrell et al. | |

FOREIGN PATENT DOCUMENTS

| | | | |
|---|---|---|---|
| EP | 1584235 | | 10/2005 |
| JP | 2001097806 A | * | 4/2001 |
| WO | 2005080481 | | 9/2005 |

* cited by examiner

*Primary Examiner* — Lorna M Douyon
*Assistant Examiner* — Tanisha Diggs
(74) *Attorney, Agent, or Firm* — Kenneth Crimaldi

(57) ABSTRACT

A composition useful for treating fabrics. The composition contains a silver-containing copolymer having polymerized units of a monomer X which is an ethylenically unsaturated compound having a substituent group selected from an unsaturated or aromatic heterocyclic group having at least one nitrogen atom and polymerized units of a monomer Y which is an ethylenically unsaturated compound selected from carboxylic acids, organosulfuric acids, sulfonic acids, phosphonic acids and esters comprising polymerized units of ethylene oxide.

6 Claims, No Drawings

METHOD FOR FABRIC TREATMENT AT LOW PH

This application claims the benefit of priority under 35 U.S.C. §119(e) of U.S. Provisional Patent Application No. 61/209,822 filed on Mar. 11, 2009.

The present invention relates to a composition useful for treating fabric at low pH. The composition contains a silver-polymer complex which is introduced into a fabric to provide a treated fabric.

Use of a silver-polymer complex in combination with any epoxy resin for fabric treatment is disclosed in U.S. Pub. No. 2008/0115291. However, use of the complex at low pH, e.g., below 8, is difficult due to precipitation of the complex. Alternative methods that are more suitable at low pH values for introducing silver into fabrics are needed.

The problem addressed by this invention is to provide a composition that is capable of introducing a biocidal silver material to a fabric at low pH to provide a treated fabric resistant to removal of biocide by laundering.

The present invention is directed to a composition useful for treating fabric. The composition comprises a complex of silver ion with a copolymer; said copolymer comprising: (a) 60-95 wt % polymerized units of a monomer X which is an ethylenically unsaturated compound having a substituent group selected from an unsaturated or aromatic heterocyclic group having at least one nitrogen atom; and (b) 5-40 wt % polymerized units of a monomer Y which is an ethylenically unsaturated compound selected from carboxylic acids, organosulfuric acids, sulfonic acids, phosphonic acids and esters comprising polymerized units of ethylene oxide. The invention is further directed to a method for treating fabric by contacting the fabric with the composition, preferably in an aqueous medium.

The term "copolymer" as used herein and in the appended claims refers to polymers polymerized from at least two different monomers. All percentages herein are by weight (wt %), unless specified otherwise. Percentages of monomers are based on total copolymer weight.

The term "aqueous" as used herein and in the appended claims means water and mixtures composed substantially of water and water miscible solvents. Fabric material suitable for treatment according to this invention includes, e.g., silk, cotton, wool, flax, fur, hair, cellulose, ramie, hemp, linen, wood pulp, polyolefins, such as polyethylene, polypropylene and polybutylene; halogenated polymers, such as polyvinyl chloride; polyaramids, such as poly-p-phenyleneteraphthalamid (e.g. KEVLAR® fibers available from DuPont), poly-m-phenyleneteraphthalamid (e.g., NOMEX® fibers available from DuPont); melamine and melamine derivatives (e.g., BASOFIL® fibers available from Basofil Fibers, LLC); polyesters, such as polyethylene terephthalate, polyester/polyethers; polyamides, such as nylon 6 and nylon 6,6; polyurethanes, such as TECOPHILIC® aliphatic thermoplastic polyurethanes available from Noveon; acetates; rayon acrylics; and combinations thereof. Preferred fabrics include cotton, polyester, cotton-polyester blends and polyolefins. In some embodiments of the invention, the fabric comprises at least 40% polyester fibers, alternatively at least 50%, alternatively at least 60%, alternatively at least 70%, alternatively at least 80%, alternatively at least 90%.

The use of the term "(meth)" followed by another term such as acrylic, acrylate, acrylamide, etc., as used herein and in the appended claims, refers to, for example, both acrylic and methacrylic; acrylate and methacrylate; acrylamide and methacrylamide; etc.

The glass transition temperature ("Tg") for the copolymers of the present invention may be measured by differential scanning calorimetry (DSC) taking the mid-point in the heat flow versus temperature transition as the Tg value.

In some embodiments of the present invention, the copolymer comprises at least 65 wt % residues of monomer X, alternatively at least 67 wt %, alternatively at least 69 wt %, alternatively at least 71 wt %. In some aspects of these embodiments, the copolymer comprises no more than 92 wt % residues of monomer X, alternatively no more than 90 wt %, alternatively no more than 88 wt %, alternatively no more than 86%, alternatively no more than 84 wt %, alternatively no more than 82 wt %; in some embodiments, the copolymer comprises no more than 35% residues of monomer Y, alternatively no more than 33 wt %, alternatively no more than 31 wt %, alternatively no more than 29 wt %; alternatively at least 8 wt % residues of monomer Y, alternatively at least 10 wt %, alternatively at least 12 wt %, alternatively at least 14 wt %, alternatively at least 16 wt %, alternatively at least 18 wt %.

In some embodiments of the present invention, monomer X is selected from vinylimidazoles, vinylimidazolines, vinylpyridines, vinylpyrroles, derivatives thereof and combinations thereof. In some aspects of these embodiments, monomer X is selected from vinylimidazoles, vinylpyridines, derivatives thereof and combinations thereof. In some aspects of these embodiments, monomer X is selected from N-vinylimidazole, 2-vinylpyridine, 4-vinylpyridine and combinations thereof. In some aspects of these embodiments, monomer X is N-vinylimidazole (VI).

In some embodiments of the present invention, monomer Y is selected from carboxylic acids, organosulfuric acids, sulfonic acids, phosphonic acids and esters of polymerized units of ethylene oxide and combinations thereof. In some embodiments of the invention, esters comprising polymerized units of ethylene oxide comprise at least 2 units of ethylene oxide, alternatively at least 3, alternatively at least 4, alternatively at least 5, alternatively at least 6. The number of polymerized ethylene oxide units is calculated from the Mn of the polymerized ethylene oxide chain. In some embodiments of the invention, the esters of polymerized units of ethylene oxide are (meth)acryloyl esters. In some embodiments of the invention, polymerized units of ethylene oxide may be capped with a $C_1$-$C_6$ alkyl group on one end. In some embodiments of the invention, polymerized units of ethylene oxide have Mn from 100 to 3000. In some embodiments of the invention, the polymerized units of ethylene oxide have Mn from 200 to 1000, alternatively from 250 to 600, alternatively from 300 to 500. In some embodiments of the invention, monomer Y is selected from acrylic acid (AA), methacrylic acid (MAA), itaconic acid, maleic acid, fumaric acid, 2-acrylamido-2-methylpropanesulfonic acid and its sodium salt and combinations thereof. In some aspects of these embodiments, the copolymer further comprises other ethylenically unsaturated monomers, e.g., (meth)acrylate esters, vinyl esters, (meth)acrylamides. Small amounts of hydrophobic monomers, e.g., higher alkyl (meth)acrylates (e.g., C-4 and higher), may be present to the extent they do not compromise water solubility. (Meth)acrylate esters may include esters of mixed ethylene/propylene oxides, providing that ethylene oxide residues are at least 50 wt % of the ethylene/propylene oxide residues (alternatively at least 75%, alternatively at least 90%) or that the esters of mixed ethylene/propylene oxide residues are no more than 20 wt % of the copolymer, alternatively no more than 15%, alternatively no more than 10%. In some embodiments of the invention, mixed ethylene/propylene oxide residues have Mn of at least 150, alternatively at least 300.

In some embodiments of the present invention, the method uses a copolymer comprising no more than 5 wt % of units derived from ethylenically unsaturated monomer containing an epoxide function. In some aspects of these embodiments, the copolymer comprises no more than 1 wt % of units derived from ethylenically unsaturated monomer containing an epoxide function. In some aspects of these embodiments, the copolymer comprises no more than 0.5 wt % of units derived from ethylenically unsaturated monomer containing an epoxide function. In some aspects of these embodiments, the copolymer comprises no more than 0.1 wt % of units derived from ethylenically unsaturated monomer containing an epoxide function. In some aspects of these embodiments, the copolymer comprises no more than 0.05 wt % of units derived from ethylenically unsaturated monomer containing an epoxide function.

In some embodiments of the present invention, the composition comprising a copolymer has a pH of at least 3, alternatively at least 4, alternatively at least 4.5. In some embodiments, the composition has a pH no greater than 7, alternatively no greater than 6, alternatively no greater than 5.5. In some embodiments, the composition has a pH of 4-6, alternatively from 4.5-5.5.

In some embodiments of the present invention, the composition comprises a latex copolymer which has at least 20 wt % solids. In some aspects of these embodiments, the latex copolymer comprises at least 25 wt % solids. In some aspects of these embodiments, the latex copolymer comprises at least 30 wt % solids.

In some embodiments of the present invention, the composition comprises polymerized units derived from a crosslinker. Crosslinkers suitable for use with the present invention include multi-ethylenically unsaturated monomers. In some aspects of these embodiments, the crosslinker derived units are derived from crosslinker selected from 1,4-butanediol diacrylate; 1,4-butanediol dimethacrylate; 1,6-hexanediol diacrylate; 1,1,1-trimethylol propane triacrylate; 1,1,1-trimethylol propane trimethacrylate; allyl methacrylate; divinylbenzene; and N-allyl acrylamide. In some aspects of these embodiments, the crosslinker derived units are derived from crosslinker selected from 1,1,1-trimethylol propane trimethacrylate. In some aspects of these embodiments, the composition comprises 0.01 to 10 wt % (based on solids) crosslinker. In some aspects of these embodiments, the composition comprises 0.01 to 5 wt % (based on solids) crosslinker. In some aspects of these embodiments, the composition comprises 0.01 to 1 wt % (based on solids) crosslinker.

In some embodiments of the invention, the copolymer comprises from 1 wt % to 50 wt % silver, based on total copolymer weight including silver, alternatively from 2 wt % to 40 wt %, alternatively from 3 wt % to 20 wt %, alternatively from 5 wt % to 15 wt %. Silver is in the form of Ag(I) ion, which typically is introduced in the form of silver nitrate. Methods for preparation of the copolymer have been disclosed previously, e.g., in U.S. Pat. Appl. Pub. No. US 2005/0227895, and also in the Examples herein. In some embodiments of the invention, to increase retention of silver by the treated fabric, additional copolymer is added which is not complexed with silver; and/or other amine compounds or polymers may be added. In some embodiments of the invention, the fabric treatment includes an epoxy resin, a polyurethane, or a combination thereof.

In some embodiments of the invention, an epoxy resin comprises at least a difunctional epoxy compound, i.e., a compound having at least two epoxy groups per molecule. In some aspects of these embodiments, the epoxy resin comprises bis-glycidyl ethers or esters, triglycidyl isocyanurate, 1-epoxyethyl-3,4-epoxycyclohexane, vinylcyclohexene dioxide, diglycidyl esters of dicarboxylic acids, diglycidyl ethers of diols, triols or polyols. Suitable examples of bis-glycidyl esters and ethers include bisphenol A diglycidyl ether, diglycidyl adipate; 1,4-diglycidyl butyl ether; ethylene glycol diglycidic ether; glycidyl ethers of glycerol, erythritol, pentaerythritol, trimethylol propane and sorbitol; epoxy resorcinol ethers; and diglycidyl ethers of polyethylene glycols. In some embodiments of the invention, the epoxy resin comprises a polymer of glycidyl (meth)acrylates and/or allyl glycidyl ether. In some embodiments of the invention, the epoxy resin is present in an amount that results in a 0.1:1 to 10:1 ratio of equivalents epoxide:equivalents X monomer unit. Preferably, the ratio is at least 0.2:1, alternatively at least 0.3:1, alternatively at least 0.5:1, alternatively at least 0.8:1. Preferably, the ratio is no more than 7:1, alternatively no more than 5:1, alternatively no more than 4:1, alternatively no more than 3:1.

In some embodiments of the invention, an amine curing agent in addition to the copolymer is used. Such amine curing agents are well known in the art and are described, e.g., in WO 2005/080481. These curing agents include polyfunctional primary and secondary amines and some tertiary amines, including amine-containing polymers.

In some embodiments of the invention, a polyester polyurethane contains polymerized residues of a polyester polyol and a diisocyanate. The diisocyanate may be an aromatic diisocyanate, e.g., toluene diisocyanate (TDI), diphenyl methane diisocyanate (MDI), p-xylylene diisocyanate, tetramethylxylene diisocyanate, isomers thereof or mixtures thereof; or an aliphatic diisocyanate, e.g., 1,6-hexamethylene diisocyanate, hydrogenated methylenediphenyl diisocyanate (HMDI), ethylene diisocyanate, isophorone diisocyanate, cyclohexane-1,4-diisocyanate, or a mixture thereof. Among the aromatic diisocyanates, MDI is preferred, especially a mixture of 4,4' and 2,4' isomers. Preferred aliphatic diisocyanates include, e.g., 1,6-hexamethylene diisocyanate, hydrogenated methylenediphenyl diisocyanate (HMDI), isophorone diisocyanate and mixtures thereof. Polyester polyols include, e.g., hydroxyl terminated products of polyhydric alcohols such as ethylene glycol, propylene glycol, diethylene glycol, neopentyl glycol, trimethylol propane, glycerol, pentaerythritol, 1,4-butanediol, 1,6-hexanediol, furan dimethanol, cyclohexane 1,6-dimethanol, diols made from dimethyl carbonate and any of the above polyhydric alcohols or mixtures thereof with polycarboxylic acids or lactones, especially dicarboxylic acids such as succinic acid, adipic acid, glutaric acid, phthalic acids and caprolactone. Preferred polyester polyols include, e.g., those formed from adipic acid and diols selected from hexanediol, ethylene glycol, 1,4-butanediol, propylene glycol and cyclohexane-1,6-dimethylol. Preferably polyhydric alcohols having more than two hydroxyl groups are present to the extent of no more than 2 wt % of the polyol, alternatively no more than 1 wt %, alternatively no more than 0.5 wt %. In some embodiments of the invention, the polyurethane has Mn from 10,000 to 100,000 and Mw from 200,000 to 2,000,000 In some embodiments of the present invention, the polyester polyurethane is an aliphatic polyester polyurethane, i.e., it contains polymerized residues of an aliphatic polyester polyol and an aliphatic diisocyanate.

Some embodiments of the present invention will now be described in detail in the following Examples. All fractions and percentages set forth below in the Examples are by weight unless otherwise specified.

EXAMPLE A

A sample of 90% vinyl imidazole (VI)/10% Acrylic Acid (AA) polymer was prepared according to the following procedure. After heating a 1 L reaction vessel containing 220 ml deionized water (DiW) under nitrogen, to 85° C., a solution consisting of 79.7 g DiW, 2.1 g of 29% aqueous ammonia, and 4.62 g of Vazo-68 (4,4'-Azobis[4-cyanopentanoic acid], CAS #2638-94-0), was added to the reaction vessel at 0.58 g/min for 150 minutes. After 5 minutes, a solution of 207.7 g DiW, 138.5 g vinyl imidazole (CAS #1072-63-5), and 15.4 g acrylic acid (AA, CAS #79-10-7) was fed into the reaction flask at 3.0 g/min for 120 minutes, followed by a DiW rinse of 144 g fed at 4.8 g/m for 30 min. The reaction mixture was held at 85° C. for 15 minutes, and a second mixture of 34.5 g DiW, 0.48 g of 29% aqueous ammonia, and 0.77 g of Vazo-68, was added to the reaction vessel at 0.34 g/min for 90 minutes, followed by a hold of 30 min at 85° C., and a rinse of 32 g DiW. The mixture was then cooled to room temperature, resulting in a clear, pale yellow solution of pH 7.6, viscosity 124 cPs, and 20.5% Solids.

EXAMPLE B

A sample of 90% vinyl imidazole (VI)/10% Poly(ethylene glycol) methyl ether methacrylate (MPEGMA-300) (Mn 300) polymer was prepared according to the procedure in Example A except that the monomer mixture consisted of a solution of 207.7 g DiW, 138.5 g vinyl imidazole, and 15.4 g poly(ethylene glycol) methyl ether methacrylate (CAS #26915-72-0, typical Mn=300). All other conditions remained the same as in Example A. The resulting polymer mixture was then cooled to room temperature, giving a clear, pale yellow solution of pH 9.1, viscosity 184 cPs, and 20.2% Solids.

EXAMPLE C

A sample of 75% vinyl imidazole (VI)/25% Poly(ethylene glycol) methyl ether methacrylate (Mn 300) polymer was prepared according to the procedure in Example A except that the monomer mixture consisted of a solution of 207.7 g DiW, 115.4 g vinyl imidazole, and 38.5 g poly(ethylene glycol) methyl ether methacrylate (CAS #26915-72-0, typical Mn=300). All other conditions remained the same as in Example A. The resulting polymer mixture was then cooled to room temperature, giving a clear, pale yellow solution of pH 9.0, viscosity 125 cPs, and 20.3% Solids.

EXAMPLE D

A sample of 50% vinyl imidazole (VI)/poly(ethylene glycol)methyl ether methacrylate (MPEGMA) (Mn 475) polymer was prepared according to the following procedure. After heating a 3 L reaction vessel containing 847.4 ml deionized water (DiW) under nitrogen, to 85° C., a solution consisting of 182 g DiW, 30.1 g of 29% aqueous ammonia, and 12.1 g of Vazo-68 (4,4'-Azobis[4-cyanopentanoic acid], CAS #2638-94-0), was added to the reaction vessel at 1.4 g/min for 150 minutes. Simultaneously a solution of 80.2 g DiW, 200.1 g vinyl imidazole (CAS #1072-63-5), and 200.2 g MPEGMA (CAS #26915-72-0, Mn=474)) was fed into the reaction flask at 4.0 g/min for 120 minutes, followed by a DiW rinse of 200 g fed at 4.8 g/m for 30 min. The reaction mixture was held at 85° C. for 15 minutes, and a second mixture of 40.1 g DiW, 10.3 g of 29% aqueous ammonia, and 2.1 g of Vazo-68, was added to the reaction vessel at 0.34 g/min for 90 minutes, followed by a hold of 120 min at 85° C., and a rinse of 32 g DiW. The mixture was then cooled to room temperature, resulting in a clear, pale yellow solution of pH 7.6, and 20.5% Solids.

EXAMPLE E

A sample of 75% vinyl imidazole (VI)/25% MPEGMA (Mn 475) polymer was prepared according to the procedure in Example D except that the monomer mixture consisted of a solution of 480.5 g DiW, 300.1 g vinyl imidazole, and 100.2 g MPEGMA (CAS #26915-72-0, typical Mn=475). All other conditions remained the same as in Example A. The resulting polymer mixture was then cooled to room temperature, giving a clear, pale yellow solution of pH 9.0 and 20.3% solids.

EXAMPLE F

A sample of 90% vinyl imidazole (VI)/10% sodium salt of 2-acrylamido-2-methylpropane sulfonic acid (Na AMPS) [5165-97-9] polymer was prepared according to the following procedure. After heating a 1 L reaction vessel containing 220 ml deionized water (DiW) under nitrogen, to 85° C., a solution consisting of 79.7 g DiW, 2.1 g of 29% aqueous ammonia, and 4.62 g of Vazo-68 (4,4'-Azobis[4-cyanopentanoic acid], CAS #2638-94-0), was added to the reaction vessel at 0.62 g/min for 140 minutes. After 5 minutes, a solution of 192 g DiW, 138.5 g vinyl imidazole (CAS #1072-63-5), and 30.8 g Na AMPS (50% aqueous solution) was fed into the reaction flask at 3.0 g/min for 120 minutes, followed by a DiW rinse of 65 g fed at 3.3 g/m for 20 min. The reaction mixture was held at 85° C. for 30 minutes, and a second mixture of 34 g DiW, 0.35 g of 29% aqueous ammonia, and 0.77 g of Vazo-68, was added to the reaction vessel at 0.39 g/min for 90 minutes, followed by a hold of 30 min at 85° C., and a rinse of 32 g DiW. The mixture was then cooled to room temperature, resulting in a clear, pale yellow solution of pH 9.4, viscosity 136 cPs, and 20.4% solids.

EXAMPLE G

A sample of 60% vinyl imidazole (VI)/40% Poly(ethylene glycol) methyl ether methacrylate (Mn 300) polymer was prepared according to the procedure in Example D except that the monomer mixture consisted of a solution of 207.7 g DiW, 92.3 g vinyl imidazole, and 61.6 g poly(ethylene glycol) methyl ether methacrylate (CAS #26915-72-0, typical Mn=300). All other conditions remained the same as in Example F. The resulting polymer mixture was then cooled to room temperature, giving a clear, pale yellow solution of pH 9.0, viscosity 77 cPs, and 19.9% solids.

General Sample Preparation Procedure: The wet pick-up of the substrate to be treated was determined using standard tap water. The measured wet pick-up was used to determine the amount of silver-containing copolymer required in the bath solution to provide the desired dry treatment level on the substrate. The appropriate weight of silver-containing copolymer was added to tap water (pH is ~2) and then pH adjusted to pH ~5 using a base (AMP-95 or 25% sodium carbonate solution). Other ingredients were added at appropriate levels—the solution was mixed using a standard air mixer until homogeneous. When the polyurethane additive is used it is added after the silver-containing polymer has been added and then the pH adjustment is made. The substrate to be treated was passed through the bath solution and then passed through two nips rolls to express excess solution. The treated, dried substrate is washed as noted, and then submitted for Ag content and/or efficacy testing.

The amount of epoxy resin was measured in equivalents epoxy group/equivalent of VI unit in the silver-containing copolymer. The fabric substrate used for the testing was 100% polyester knit fabric, 3.5 oz/yd$^2$ (125 g/m$^2$) basis weight.

Examples of Low pH Silver-Polymer Formulations in Water

TABLE 1

Different silver-containing polymer solutions

| poly. | g | Polymer composition (% solids) | 70% HNO$_3$ (g) | AgNO$_3$ (g) | 35% H$_2$O$_2$ (g) | Ag$^1$ (%) | Color$^2$ |
|---|---|---|---|---|---|---|---|
| 1 | 75 | 50 VI/ 50 PEGMA$_{475}$ (24%) | 11 + 25 H$_2$O | 3.3/2 g H$_2$O | 0.3 | 2.0 (anal) | 3 |
| 2 | 50 | 75 VI/ 25 PEGMA$_{475}$ (24%) | 10 + 50 H$_2$O | 3.3 g in 2 g H$_2$O | 0.3 | 2.5 (anal) | 0 |
| 3 | 75 | 50 VI/ 50 PEGMA$_{475}$ (24%) | 11 | 4.1 g in 5 g H$_2$O | 0.3 | 3.0 (anal) | 3 |
| 4 | 75 | 50 VI/ 50 PEGMA$_{475}$ (20.5%) | 11 | 2.7 g in 5 g H$_2$O | 0.3 | 2.08 (anal) | 3 |
| 5 | 50 | 75 VI/ 25 PEGMA$_{475}$ (20.5%) | 11 | 2.7 g in 6 g H$_2$O | 0.3 | 2.79 (anal) | 0 |
| 6 | 50 | 90 VI/ 10 PEGMA$_{300}$ (20.2%) | 10 | 2.7 g in 5 g H$_2$O | 0.4 | 2.6 (calc) | 0 |
| 7 | 50 | 90 VI/10 AA (20.5%) | 9 | 2.7 g/5 g H$_2$O | 0.4 | 3.0 (calc) | 0 |
| 8 | 50 | 75 VI/ 25 PEGMA$_{300}$ (20.3%) | 10 | 2.7 g/3 g H$_2$O | 0.4 | 2.7 (calc) | 0 |
| 9 | 50 | 75 VI/ 25 PEGMA$_{475}$ (24%) | 11 | 2.7 g/6 g H$_2$O | 0.3 | 3.1 (calc) | 0 |
| 10 | 100 | 75 VI/ 25 PEGMA$_{475}$ (24%) | 22 | 5.4 g/10 g H$_2$O | 0.8 | 3.0 (calc) | 0 |
| 11 | 50 | 90 VI/ 10 AMPS-Na (20.4%) | 9 | 2.73 g/5 g H$_2$O | 0.4 | 3.0 (calc) | 0 |
| 12 | 60 | 60 VI/ 40 PEGMA$_{300}$ (19.9%) | 10 | 2.0 g/2 g H$_2$O | 0.5 | 2.1 (calc) | 2 |

$^1$anal = analyzed by Inductively Coupled Plasma, calc = calculated
$^2$This denotes color of the solution (0 = no color, 5 = dark red color) when the formulation is diluted in tap water (Ag$^+$ = 300 ppm), the pH adjusted to 5 with base and kept under ambient light for 24 h

TABLE 2

Incorporation of silver-containing polymer into 100% polyester fabric

| | poly. | g | H$_2$O (g) | base (g) | epoxy (g) | PU (g) | soft. (g) | pH | Ag, ppm |
|---|---|---|---|---|---|---|---|---|---|
| 1 | 9 | 2.5 | 347.23 | B1 (0.24) | none | none | none | 5.5 | 278 |
| 2 | 9 | 2.5 | 346.41 | B1 (0.30) | E1 (0.76) | none | none | 5.3 | 274 |
| 3 | 9 | 2.5 | 339.31 | B1 (0.31) | none | PU1 (7.85) | none | 5.3 | 286 |
| 4 | 9 | 2.5 | 338.58 | B1 (0.28) | E1 (0.76) | PU1 (7.85) | none | 5.1 | 309 |
| 5 | 9 | 0.6 | 499.16 | B1 (0.07) | E1 (0.17) | none | none | 5.0 | * |
| 6 | 9 | 1.2 | 498.29 | B1 (0.16) | E1 (0.35) | none | none | 5.0 | * |
| 7 | 9 | 3.62 | 494.78 | B1 (0.5) | E1 (1.10) | none | none | 5.0 | * |
| 8 | 10 | 2.17 | 297.63 | B1 (0.2) | none | none | none | 4.95 | 352 |
| 9 | 10 | 2.17 | 293.11 | B1 (0.2) | none | PU2 (4.52) | none | 5.12 | 300 |
| 10 | 10 | 2.17 | 292.48 | B1 (0.2) | E1 (0.63) | PU2 (4.52) | none | 4.99 | 365 |
| 11 | 10 | 2.17 | 293.11 | B1 (0.2) | none | PU3 (4.52) | none | 5.24 | 279 |
| 12 | 10 | 2.17 | 292.48 | B1 (0.2) | E1 (0.63) | PU3 (4.52) | none | 5.18 | 322 |
| 13 | 10 | 1.84 | 297.02 | B2 (0.61) | E1 (0.53) | none | none | 5.13 | 273 |
| 14 | 10 | 1.84 | 293.21 | B2 (0.59) | E1 (0.53) | PU2 (3.83) | none | 5.15 | 252 |
| 15 | 10 | 1.84 | 288.37 | B2 (0.61) | none | none | S1 (9.18) | 5.01 | 259 |
| 16 | 10 | 1.84 | 284.12 | B2 (0.50) | E1 (0.53) | PU2 (3.83) | S1 (9.18) | 5.02 | 214 |
| 17 | 10 | 1.84 | 288.55 | B2 (0.43) | none | none | S2 (9.18) | 5.11 | 255 |
| 18 | 10 | 1.84 | 284.13 | B2 (0.49) | E1 (0.53) | PU2 (3.83) | S2 (9.18) | 5.08 | 240 |

TABLE 2-continued

Incorporation of silver-containing polymer into 100% polyester fabric

| | poly. | H$_2$O g (g) | base (g) | epoxy (g) | PU (g) | soft. (g) | pH | Ag, ppm |
|---|---|---|---|---|---|---|---|---|
| 19 | 10 | 1.84 | 288.43 B2 (0.55) | none | none | S3 (9.18) | 5.06 | 237 |
| 20 | 10 | 1.84 | 284.07 B2 (0.55) | E1 (0.53) | PU2 (3.83) | S3 (9.18) | 5.15 | 240 |
| 21 | 10 | 1.84 | 292.99 B2 (0.58) | none | none | S4 (4.59) | 4.91 | 241 |
| 22 | 10 | 1.84 | 288.68 B2 (0.53) | E1 (0.53) | PU2 (3.83) | S4 (4.59) | 5.00 | 234 |

*silver level not determined
E1 is GE-30 (Erisys Co.; trimethylolpropane triglycidyl ether)
B1 is AMP-95 (2-amino-2-methyl-1-propanol)
B2 is 25% aq. Na$_2$CO$_3$
PU1 is PERMAX 200 (aliphatic polyurethane dispersion from Lubrizol Corp.)
PU2 is BAYHYDROL 140AQ (polyurethane dispersion from Bayer MaterialScience)
PU3 is BAYHYDROL 402A (polyurethane dispersion from Bayer MaterialScience)
S1 is EVOSOFT WOR (hydrophilic silicone softener; pH 2-3; cationic (Dystar Co.))
S2 is EVOSOFT LDS (quaternary amide; pH 4.5-5.5; cationic (Dystar Co.))
S3 is EVOSOFT HSP (hydrophilic micro silicone emulsion softener; pH 4-6; weakly cationic (Dystar Co.))
S4 is LAVASOFT MEC (aminofunctional silicone; concentrated; pH 6-7; weakly cationic (Dystar Co.))

TABLE 3

Color and brightness of silver containing fabric after exposure to cold white fluorescent (CWF) light

| Sample (no. in Table 2) | Hunter Lab/ Brightness* | | |
|---|---|---|---|
| | Initial | 1 wk CWF Exposed | Unexposed |
| No Treatment | 89.30, +2.79, −7.20 88.70 | 89.01, +2.84, −7.29 88.22 | 88.83, +2.86, −7.30 87.88 |
| 13 | 88.88, +2.83, −7.95 88.80 | 89.47, +2.83, −7.96 90.02 | 89.30, +2.85, −8.03 89.78 |
| 14 | 88.77, +2.76, −7.80 88.54 | 89.10, +2.80, −7.84 89.21 | 88.71, +2.85, −8.10 88.80 |
| 15 | 89.02, +2.72, −7.77 88.92 | 89.22, +2.85, −7.95 89.52 | 89.10, +2.86, −8.01 89.39 |
| 16 | 88.72, +2.77, −7.45 87.99 | 89.14, +2.77, −7.56 88.86 | 88.92, +2.78, −7.43 88.29 |
| 17 | 89.03, +2.67, −7.44 88.55 | 88.83, +2.79, −7.79 88.59 | 89.36, +2.73, −7.69 89.46 |
| 18 | 88.67, +2.73, −7.41 87.82 | 88.66, +2.77, −7.45 87.80 | 88.32, +2.77, −7.53, 87.27 |
| No treatment | 88.86, +2.89, −7.51 88.32 | 89.12, +2.81, −7.83 89.07 | 89.03, +2.86, −7.89 88.96 |
| 19 | 88.86, +2.89, −7.51 88.32 | 89.12, +2.81, −7.83 89.07 | 89.03, +2.86, −7.89 88.96 |
| 20 | 88.90, +2.89, −7.50 88.37 | 89.49, +2.76, −7.81 89.79 | 89.35, +2.93, −8.14 89.88 |
| 21 | 88.78, +2.85, −7.64 88.36 | 89.64, +2.80, −7.70 89.93 | 89.28, +2.80, −7.83 89.40 |
| 22 | 88.60, +2.87, −7.35 87.61 | 89.18, +2.84, −7.76 89.07 | 89.24, +2.77, −7.67 89.12 |

*4 plies using Brightmeter Micro S-5

Antimicrobial efficacy of silver containing fabric. The bacteriostatic activity of some of the treated polyester fabric was measured using AATCC Method 100. The test samples were quantitatively evaluated for bacteriostatic activity by placing 1.0 ml of a diluted culture of the test bacterial (10$^5$ organisms) in direct contact with the sample. Following a 24 hour incubation period at 35° C., the samples were diluted with Dey Enley broth (DE broth) and the number of surviving organisms was determined by the standard plate count. The percent reduction was calculated by comparison to the number of organisms recovered at zero contact time. The results of these analyses are provided in Table 4.

TABLE 4

Antimicrobial efficacy of silver containing fabrics

| | Log Reduction (cfu/sample) | |
|---|---|---|
| Experiment ID (from Table 2) | S. aureus (ATCC# 6538) | K. pneumoniae (ATCC# 4352) |
| no treatment | −3.3 | −3.8 |
| 5 | 2.3 | 3.9 |
| 6 | >3.8 | >3.9 |
| 7 | >3.8 | >3.9 |

The invention claimed is:

1. A composition useful for treating fabric; said composition having a pH from 3 to 6 and comprising a complex of silver ion with a copolymer; said copolymer comprising: (a) 60-90 wt % polymerized units of a monomer X which is N-vinylimidazole; and (b) 10-40 wt % polymerized units of a monomer Y which is an ethylenically unsaturated compound selected from carboxylic acids, sulfonic acids, and esters comprising polymerized units of ethylene oxide; wherein the copolymer comprises 5 wt % to 15 wt % silver, based on total copolymer weight.

2. The composition of claim 1, wherein monomer Y comprises an ethylenically unsaturated compound selected from (meth)acrylic acid, (meth)acrylic esters of at least 2 polymerized ethylene oxide residues and (meth)acryloyl esters comprising sulfonic acid functionality.

3. The composition of claim 2, wherein the copolymer comprises 65-90 wt % polymerized units of monomer X and 10-35 wt % polymerized units of monomer Y.

4. The composition of claim 3 having a pH from 3 to 5.5.

5. The composition of claim 4 in which monomer Y is selected from esters of polymerized units of ethylene oxide comprising at least 3 units of ethylene oxide, wherein the polymerized units of ethylene oxide are capped with a C$_1$-C$_6$ alkyl group on one end.

6. The composition of claim 5 in which the polymerized units of ethylene oxide have Mn from 250 to 600.

* * * * *